United States Patent [19]

Hall, II et al.

[11] Patent Number: 5,344,652
[45] Date of Patent: Sep. 6, 1994

[54] ANTICORROSIVE MICROBICIDE

[75] Inventors: Robert T. Hall, II, Welch; Jo-Ann B. Maltais, Minneapolis; Louis C. Cosentino, Plymouth, all of Minn.

[73] Assignee: Minntech Corporation, Minneapolis, Minn.

[21] Appl. No.: 778,940

[22] Filed: Dec. 10, 1991

[30] Foreign Application Priority Data

Apr. 5, 1990 [WO] PCT Int'l Appl. ............... PCT/US90/01862

[51] Int. Cl.$^5$ ............................................. A01N 25/00
[52] U.S. Cl. .................................... 424/405; 424/616; 252/95; 252/186.23
[58] Field of Search ................ 424/616, 405; 514/129, 514/134; 252/186.23, 95

[56] References Cited

U.S. PATENT DOCUMENTS

| | | | |
|---|---|---|---|
| 2,284,477 | 5/1942 | Reichert et al. | 260/502 |
| 2,814,641 | 11/1957 | Phillips et al. | 260/502 |
| 3,679,587 | 7/1972 | Smith | 252/75 |
| 4,051,058 | 9/1977 | Bowing et al. | 252/186 |
| 4,051,059 | 9/1977 | Bowing et al. | 252/186 |
| 4,051,059 | 9/1977 | Bowing et al. | 252/186 |
| 4,477,438 | 10/1984 | Wilcockson et al. | 424/252 |
| 4,731,222 | 3/1988 | Kralovic et al. | 422/204 |
| 4,743,447 | 5/1988 | Le Rouzic | 424/130 |
| 5,077,008 | 12/1992 | Kralovic et al. | 422/252 |

FOREIGN PATENT DOCUMENTS

| | | |
|---|---|---|
| 8930788 | 3/1990 | European Pat. Off. . |
| 7108120 | 12/1971 | France . |
| 1079102 | 6/1989 | Japan . |
| 1240226 | 7/1971 | Sweden . |
| 2025229 | 1/1980 | United Kingdom . |

OTHER PUBLICATIONS

Product brochure for VICTAWET ® 35B, 58B, 85X by Akzo Chemicals Ltd. Oct. 1988.
Product brochure "Fluorad TM"—Fluorochemical Surfactants by 3M Industrial Products Division, issued Mar. 1988.
Product brochures from Actril ®, Renalin ®, and Minncare ® available from Minntech Corporation (Date unknown) 1991.
Product brochure for TERG-A-Zyme ® "How To Clean With ALCONOX ®—Liqui-Nox ®—Terg-A-Zyme ®" by Alconox, Inc. date unknown.
"The Performance of Aluminum with Specific Chemicals" pp. 928–930 from Resistance of Aluminum Alloys to Corrosion date unknown.
"Corrosion Resistance of Aluminum and Aluminum Alloys" by Hollingsworth and Hunsicker, pp. 204, 225, 231 and 234 date unknown.
Product brochure for ProtoZyme ® by RUHOF, date unknown, author unknown, no page numbers.
PCT Notification of Transmittal of International Preliminary Examination Report—Nov. 23, 1992.
European Search Report—Jan. 15, 1993 (with documents listed above).

*Primary Examiner*—Marianne M. Cintins
*Assistant Examiner*—K. Weddington
*Attorney, Agent, or Firm*—Barbara A. Wrigley

[57] ABSTRACT

A stable, shippable microbicide solution, having improved anticorrosive properties comprising a two part system, the first part consists of a mixture of acetic acid, hydrogen peroxide, peracetic acid, and water. This is referred to for brevity as a peroxide/peracid solution. The second consists of water having dissolved therein a wetting agent which is preferably Victawet ® 35B which is the sodium hydroxide reaction product of an aliphatic alcohol and phosphorous pentoxide. Three other Victawet ® agents have proven operative. Alternatively, Fluorad TM FC95, which is a agent of potassium perfluoroalkyl sulfonates may be used. The microbicide may also be a premixed one component system containing the anticorrosive agents of the invention.

24 Claims, No Drawings

ANTICORROSIVE MICROBICIDE

FORWARD

The present invention is an improvement over biocides such as those disclosed in copending U.S. application number PCT/US87/01147, filed May 14, 1987 assigned to the same assignee as the present invention. The disclosure of PCT/87/01147 is incorporated herein by reference. Such compositions of biocides of mixtures of hydrogen peroxide, peracetic acid and acetic acid will be referred to herein as peroxide/peracid solutions. The formulations of the prior art peroxide/peracid type including those of the co-pending application are made substantially less corrosive through the present invention. Certain sequestering agents and/or catalysts for the formation of peracetic acid may increase the corrosiveness of peroxide/peracid solutions. Therefore, omission of such agents or selection of sequestrating agents that do not promote corrosion are advisable.

1. Field of the Invention

This invention relates to anticorrosive microbicides having improved anticorrosive properties for sterilizing, disinfecting or cleaning and sanitizing surfaces. More particularly, it is for treating surfaces which tend to corrode when typical sterilant solutions based on peracetic acid, acetic acid and hydrogen peroxide are used.

2. Background of the Invention

Peroxide/peracid containing compositions have found extensive use as microbicides due to their biocidal activities. An undesirable characteristic of prior art peroxide/peracid compositions, including those of the co-pending application, is the tendency to bring about corrosion of the metal of instruments and surfaces when treated with these compositions. In the case of medical or dental instruments which are frequently aluminum or brass, often plated with an ornamental and protective layer of nickel or nickel and/or chromium, these plated surfaces and the underlying base metals tend to corrode at an unacceptable rate in prior art peroxide/peracid solutions. The intended usage of such microbicides for sterilization is desirably at a temperature above room temperature and optimally at about 50° C. Increasing temperature accelerates corrosion by these prior art biocides. Peroxide/peracid microbicide solutions are effective at 20° C. but are notably slower in their rate of sterilization at such lower temperatures.

A need exists for a microbicide which can be shipped in sealed containers, is stable during shipping and storage as a concentrate, and during its role in the diluted form, acts at a variety of temperatures to provide disinfection, sterilization and sanitization. There is also a need to have anticorrosive properties over wide temperature ranges for the microbicide.

SUMMARY OF THE INVENTION

The preferred form of this invention provides a new and improved microbicide solution, concentrated or premixed, having improved anticorrosive properties consisting of a combination of acetic acid, hydrogen peroxide, peracetic acid, corrosion inhibitors and water. As used herein, the term "peroxide/peracid" will refer to mixtures in solution of peracetic acid, acetic acid and hydrogen peroxide. Anticorrosive properties are obtained by inclusion of small quantities of certain agents which unexpectedly were found to function as corrosion inhibitors.

An object of the present invention is to provide a sterilant having improved anticorrosive properties for use in applications requiring sterilization, disinfection or cleaning/sanitization of metal and other surfaces including plastics over a variety of temperature ranges. This objective is met by the addition of agents which unexpectedly have been found to inhibit corrosion and which are acceptable in applications for the medical, dental and food industry.

It was unexpectedly found that Victawet ® 35B, a commercially available material offered as a agent and the preferred additive for the invention, acts to provide improved anticorrosive properties to peroxide/peracid solutions of the prior art used for microbicidal purposes. An improved result of corrosion resistance is also obtained with Fluorad TM FC95, hereinafter FC95, but not to the extent found with Victawet ® 35B or certain other Victawets ®, namely 58B and 85X. Victawet ® 35B as well as the 58B and 85X are commercially available from AKZO Chemical Company. 35B is a formulation which is the sodium hydroxide reaction products of an aliphatic alcohol and phosphorous pentoxide. Specifically, it has a composition sold under the trademark Victawet ® 35B of mono sodium salt of phosphoric acid, and mono 2-ethyl hexyl ester, (20–45%) C.A.S. Registry Number 1070-03-7, pyrophosphonic acid, bis (2-ethyl hexyl) esters, sodium salts (20–30%) C.A.S. 75212-49-6; polyphosphonic acids, 2-ethyl hexyl esters, sodium salts (10–25%) C.A.S. 68915-31-1; water (20–25%). Phosphoric acid, bis (2-ethyl hexyl) ester, sodium salt (<10%), C.A.S. 141-65-1, phosphoric acid, sodium salts, mono and/or di (<5%), C.A.S. 7558-80-7, 7558-79-4 and 2-ethyl hexanol (<3%) C.A.S. 104-76-7 may be present. This material will hereinafter for brevity be referred to by its trade name.

Fluorad TM FC95 wetting agent is an anionic fluoro chemical of potassium perfluoroalkyl sulfonate available from the 3M Company. Hereinafter, for brevity, it will be referred to as FC95.

Chemical sterilants, such as ACTRIL ®, Renalin ® and Minncare TM, microbicides of the peroxide/peracid type available from the same assignee as the present invention, do not have a corrosion inhibitor present. They also include a heavy metal sequestering agent. This is acceptable where corrosion is not a problem, i.e., in use on stainless steel or plastics. However, care must be exercised in selection of sequestrants so they do not increase corrosion.

The corrosion inhibited microbicide of the present invention is directed to uses where corrosion is or may be a problem. The peroxide/peracid compositions has added thereto material which acts as an inhibitor as will be described. The product of the preferred form of the invention may be shipped in accordance with Title 49 Code of Federal Regulations (DOT). The formulation of peroxide/peracid concentrate (Part A) and the inhibitor containing solution (Part B) have long storage stability prior to mixing. After mixing the resulting solution has a reasonable life while retaining effective microbicidal activity at room and elevated temperatures. The mixture possesses improved anticorrosive properties in the final diluted form for use as a microbicide.

In preferred form, the present invention formulation includes peracetic acid, acetic acid, hydrogen peroxide, corrosion inhibitor, and water. By use of amber glass bottles for the peroxide/peracid concentrate, and by keeping the volume of the peroxide/peracid at a low quantity (about 58 ml), it is shippable in sealed glass containers.

The peroxide/peracid solutions in which the invention finds application includes those which have concentration of active ingredients to be effective as a biocide. By use of Victawet ® (either 58B, 85X or 35B) or FC95 in such solutions (or mixtures thereof) their corrosive nature is greatly reduced. FC98 and Victawet ® 12 while reducing corrosion were deemed unsatisfactory compared with the others.

The preferred biocide of the invention as will be described below consists of a two part system to be mixed prior to use as a biocide. The first part, hereafter referred to as Part A, is the active biocide concentrate which contains the peroxide/peracid. The second part, hereafter Part B, is water or a water miscible solvent, or other compatible solvent, having an inhibitor dissolved and dispersed therein, namely, either the above identified Victawet wetting agents or 3M's Fluorad TM FC95 wetting agent or their equivalents. The Part A peroxide/peracid is a combination of acetic acid, hydrogen peroxide, peracetic acid, and water. Before use, the Part A is diluted into Part B containing the inhibitor and water and is thoroughly mixed. In actual use the concentrate above is diluted with water in Part B, preferably from about 66 to about 80 times. The recommended shelf life of the fully mixed Part A and Part B is 7 days. Therefore, as will be discussed below, this two-part system desirably will be mixed shortly before use. Other formulations of peroxide/peracid have a longer shelf life, as will be apparent from the description below.

Items to be treated can be cleaned with detergents when having soil thereon to reduce organic load to low levels. Cleaning and rinsing prolongs the effective life of the biocide of the invention and allows for greater reusability of the mixed solution. Suitable detergents are well known and include, without restriction, Tergazyme TM or Protozyme TM. It is also contemplated that the biocide of the present invention will be used in ultrasonic cleaning tanks as one application for its use. It can also be reused over a seven day period after mixing.

DETAILED DESCRIPTION OF PREFERRED EMBODIMENTS

The goal of the invention was to provide a stable, shippable, multi-purpose, reusable microbicide having improved anticorrosive properties usable over a broad temperature range. To obtain this result not only was it necessary to locate an agent or agents that substantially reduced corrosion, but ones which were also biocompatible, and compatible with peroxide/peracid microbicides. A large number of additive materials which claim to impart anti-corrosive benefits were examined, but surprisingly these proved ineffective. Unexpectedly, it was found that four commercial materials sold as wetting agents imparted a significant reduction in the corrosion of metals ordinarily attacked in peroxide/peracid solutions.

Historically, peroxide/peracid disinfectants and sterilant solutions have been too unstable for sealed container shipping due to the peroxide and peracid contents which required special handling, shipping and storage procedures. Stability of the diluted ready to use microbicide is achieved, as taught in the co-pending application, by formulating it such that the ratio of total acid (peracetic acid, acetic acid and combinations thereof) to hydrogen peroxide is between approximately 1.0 and 11. The ready to use formulations of the co-pending application, when the anticorrosive additives of the present invention are added thereto, retain their long shelf life and have reduced corrosiveness.

In the present preferred form of the invention, where a concentrate of peroxide/peracid is used stability is attained by shipping in a small quantity in amber glass bottles as a first component (Part A) with a second component (Part B) of water and inhibitor in a separate container.

After extensive investigation, it was unexpectably found that three Victawet ® agents substantially reduced the propensity of the known peroxide/peracid biocides to corrode metal surfaces of medical and dental instruments. Owing to the Victawet ® additives, the microbicide exhibits anticorrosive properties. Other agents which claim to provide corrosion inhibition did not so function with the peroxide/peracid biocides. Victawet ® 35B, 58B and 85X and to a lesser degree Fluorad FC95, which are not sold as or suggested as having the property of a corrosion inhibitor, unexpectedly did function to substantially reduce corrosion on test specimens.

Investigations revealed that of 26 agents tested, including many which claimed to be corrosion inhibitors, only four were found to be adequately effective as anticorrosive agents in peroxide/peracid formulations. None of the four were ones that were sold or promoted as anticorrosive agents. The preferred formulation was also found to be stable, shippable, and effective on dilution as a sterilant, disinfectant, virucide, fungicide, bactericide, tuberculocide, HIV killing agent and as a cleaner-sanitizer on surfaces. The preferred formulation is reusable for 7 days maintaining efficacy unless materials which significantly decompose the peracetic acid are introduced into the biocide.

Two Component Concentrate Form of the Invention

EXAMPLE I

Two separate components were formulated in the preferred form as follows:

Part A: Hydrogen peroxide and acetic acid, or hydrogen peroxide, acetic acid and peracetic acid were mixed with water to provide a concentrate solution of hydrogen peroxide, peracetic acid, acetic acid and the balance water. The mixes contained:

Hydrogen peroxide about 18 to 30% by weight
Peracetic acid from about 3% to 5%
Acetic acid from about 6% to about 10%

The resultant solutions did not contain a sequestrant as an additive. Fifty-eight (58) milliliters of concentrate of Part A was placed into four ounce amber glass bottles and sealed. Over prolonged periods, in excess of ten months, no significant deterioration occurred. Tests were conducted at 4° C., 25° C. and 35° C. Periodic analysis of the samples was made. There was a greater decrease in the concentration of the peracetic acid at the higher temperatures than at 4° C. However, the changes were within acceptable limits for efficacy of the final mixed solution.

Part B: Victawet ® 35B, the sodium hydroxide reaction products of an aliphatic alcohol (2-ethyl hexyl) and phosphorous pentoxide, was thoroughly mixed with water to a ultimate concentration of from about 0.005 to about 1.0% by weight of Victawet ® 35B. This mixture was placed in one gallon sealed containers and stored for ten months at 4° C., 25° C. and 35° C. Periodic tests of samples showed no deterioration at the end of this time at any of these storage temperatures.

Part A and Part B were thoroughly mixed in a ratio of 58 ml of Part A to one gallon of Part B. The thus diluted solutions were tested for biocidal activity and stability. The amount of corrosion of metal was determined and compared with diluted Part A control solution without the additives of Part B and with solutions prepared using in place of the Victawet ® 35B of Part B, Victawet ® 58B, 12 and 85X, and Fluorad ™ FC95 and Fluorad ™ FC98. The test metals were a dental mirror of chromium plated brass having a metal surface of about 10.9 square centimeter area, naval brass coupon and 5056 aluminum rod stock. Tests were at room temperature. Results for mirrors were as shown below:

| SOLUTION (% by wt additive) | CORROSION RATE (grams/hr) |
| --- | --- |
| Control (w/o inhibitor) | $48.8 \times 10^{-5}$ |
| Victawet ® 35B (0.025%) | $1.47 \times 10^{-5}$ |
| Victawet ® 35B (0.10%) | $1.59 \times 10^{-5}$ |
| Victawet ® 12 (0.025%) | $22.1 \times 10^{-5}$ |
| Victawet ® 12 (0.10%) | $18.5 \times 10^{-5}$ |
| Victawet ® 58B (0.025%) | $5.92 \times 10^{-5}$ |
| Victawet ® 58B (0.10%) | $<1.2 \times 10^{-5}$ |
| Victawet ® 85X (0.025%) | $8.78 \times 10^{-5}$ |
| Victawet ® 85X (0.10%) | $.39 \times 10^{-5}$ |
| FC95 (0.05%) | $6.77 \times 10^{-5}$ |
| FC95 (0.10%) | $8.13 \times 10^{-5}$ |
| FC98 (0.05%) | $21.2 \times 10^{-5}$ |
| FC98 (0.10%) | $18.3 \times 10^{-5}$ |

FC95 is a potassium perfluoroalkyl sulfonate, C.A.S. No. 2795-39-3 with possible small amounts of C.A.S. 60270-55-5, 3871-99-6, 3872-25-1, and 29420-49-3.

Victawet ® 85X has a composition of $Na_5(C_8H_{17})_5(P_3O_{10})_2$ (sodium pentakis (2-ethyl hexyl) triphosphate) and $Na_2HPO_4$ (phosphoric acid, di sodium). Victawet ® 58B is the sodium hydroxide reaction product of an aliphatic alcohol and phosporous pentoxide.

When the concentration of Victawet ® 35B was below about 0.025% the corrosion rate increased markedly although it was still much less than the rate of corrosion of the control even when the Victawet ® 35B concentration was as low as 0.005%.

FC95 has a tendency to reduce the concentration of peracetic acid so, while it has desirable corrosion inhibitor properties, it is less desirable for its effect on peracetic acid properties.

As the table above illustrates, the Victawet ® 35B, 58B and 85X containing solutions were superior to the FC95, insofar as anti-corrosive effect is concerned. The next best anticorrosive agents to FC95 of those tested were FC98 and Victawet ® 12. While providing improvement over the control these were deemed to be unacceptable.

Stability of the mixture of Parts A and B were determined by analysis of the concentration of peracetic acid and hydrogen peroxide in the test samples. Shelf life after mixing was determined to be at least 7 days even at elevated temperatures. Shelf life is the time at which the level of peracetic acid decreased to below the level where it is effective as a microbicide.

The mixed solutions of Parts A and B were tested for their efficacy as a sterilant, sporicide, virucide, bactericide, disinfectant, HIV killing agent, tuberculocide, germicidal spray, cleaner/sanitizer and fungicide on surfaces. The mixed solution proved effective at 20° C. in the undiluted condition and was reusable without replacement or addition of more solution for seven days after mixing. At 20° C. the formulation of Example I acted as a sterilant, sporicide, and virucide for Hepatitis B in less than 2.5 hours. By elevating the temperature to 50° C., the time was reduced to 10 minutes or less. Virucidal effectiveness against HIV required one minute; other viruses tested required 10 minutes or less.

As a tuberculocide only, 10 min. at 20° C. was required.

The mixed solution also is effective at 20° C. for uses such as, but not limited to a broad spectrum disinfectant, a germicidal spray and as a cleaner-sanitizer for non-food contact surfaces, all in 10 minutes or less.

EXAMPLE II

Although the preferred form of the invention is a two part system as described in Example I above, it is possible to use the peroxide/peracid solutions of the prior art and add directly to these solutions the Victawet ® 35B, 58B and 85X or the FC95 or mixtures thereof in the amounts indicated for the mixed solutions of Parts A and B. While the amounts of additive shown in the table of Example I reduce the rate of corrosion to low levels it is possible to increase the amount of additive up to their solubility level in the peroxide/peracid mixture. In a totally aqueous system, the solubility limit of Victawet ® 35B is about 1%, Victawet ® 58B is about 5% and Victawet ® 85X is about 10%. For FC95 is an aqueous system the solubility limit is about 1%. Increased quantities are possible when a co-solvent is used.

Specifically, peroxide/peracid solutions having a composition in the following ranges will have improved anticorrosive properties substantially as set forth above when blended with Victawet ® 35B, 58B or 85X so its concentration is between about 0.005% by weight up to the solubility limit. With FC95 so that its concentration is about 0.001% by weight up to its solubility limit requirement anticorrosive benefits result.

The concentrations below are those in the as stabilized state.

Hydrogen peroxide from about 0.2 to about 8% by weight

Combined acetic acid and peracetic acid from about 0.2 to 11% by weight

Balance water

Where the ratio of the combined acid to hydrogen peroxide is between about 1.0 to about 11

Following mixing of the above solutions with either Victawet ® 35B, 58B, 85X or FC95, the solutions of this example retain biocidal activities essentially as described in the co-pending application or as referred to in the prior art. The shelf life greatly exceeds that of Example I and the solution can be reused without additional biocide or replacement for prolonged periods.

The above Examples I and II are to the preferred form of the invention. It is operable to achieve the anti-corrosion advantages of the invention in microbicides of the hydrogen peroxide, peracetic acid and acetic acid types over very broad ranges of composition of those three materials. Microbicidal solutions have reduced corrosive character over a range as follows when additives in accordance with the invention are used:

$H_2O_2$ from about 0.004% to about 30% by weight peracetic acid from about 0.0003% to less than 55% by weight acetic acid from about 0.025% to about 12% by weight balance water To reduce the corrosiveness of microbicides coming within the above formulations, there is added a quantity of any one or more of the additives previously described, namely, Victawet® 35B or 58B or 85X or FC95. The quantity of the addition is limited by the solubility limits at the upper end and at the lower limit by the amount needed to achieve reduction in the corrosiveness of the microbicide. At the lowest there should be an amount of additives in excess of 0.001% by weight. When a two part system, where the additive anti-corrosive agent is to be added to the peroxide/peracid solution, then the additive may be dissolved at up to 10% by weight in a water miscible solvent or other solvent to reduce the volume of the additive part to be blended with the peroxide/peracid solution.

What is claimed is:

1. A biocide of the peroxide-peracid type having improved anticorrosive properties, said biocide having an additive selected from the group consisting of:
   (a) from about 0.005% by weight up to the solubility limit of sodium hydroxide reaction products of an aliphatic alcohol and phosphorous pentoxide;
   (b) from about 0.001% by weight up to the solubility limit a mixture of sodium pentakis (2-ethyl hexyl) triohosphate and phosphoric acid, di sodium; and
   (c) from about 0.001% by weight up to the solubility limit of potassium perfluoroalkyl sulfonate.

2. The biocide of claim 1 wherein the additive is from about 0.005% by weight up to about 1% by weight of the sodium hydroxide reaction products of an aliphatic alcohol and phosphorous pentoxide.

3. The biocide of claim 1 wherein the additive is from about 0.001% by weight up to about 10% by weight of a mixture of sodium pentakis (2-ethyl hexyl) triphosphate and phosphoric acid, disodium.

4. The biocide of claim 1 wherein the additive is from 0.001% by weight to about 1% by weight of potassium perfluoroalkyl sulfonate.

5. The biocide of claim 2 wherein the aliphatic alcohol comprises 2-ethyl hexyl alcohol.

6. The biocide of claim 5 wherein the additive comprises:
   a) 20%–45% by weight mono sodium salt of phosphoric acid, mono (2-ethyl hexyl) ester;
   b) 20%–30% by weight pyrophosphonic acid, bis (2-ethyl hexyl) esters, sodium salts;
   c) 10%–25% by weight polyphosphonic acids, 2-ethyl hexyl esters, sodium salts;
   d) 20%–25% by weight water;
   e) less than 10% by weight phosphoric acid, bis (2-ethyl hexyl) ester, sodium salt;
   f) less than 3% by weight 2-ethyl hexanol; and
   g) less than 5% by weight phosphoric acid, sodium salts, mono and di.

7. The biocide of claim 1 wherein the additive is potassium perfluoroalkyl sulfonate.

8. The biocide of claim 1 wherein the additive comprises:
   a) 20%–45% by weight mono sodium salt of phosphoric acid, mono (2-ethyl hexyl) ester;
   b) 20%–30% by weight pyrophosphonic acid, bi (2-ethyl hexyl) esters, sodium salts;
   c) 10%–25% by weight polyphosphonic acids, (2-ethyl hexyl) esters;
   d) less than 10% by weight phosphoric acid, bis (2-ethyl hexyl) ester, sodium salt;
   e) less than 3% by weight 2-ethyl hexanol;
   f) less than 5% by weight phosphoric acid, mono and di sodium salts; and
   g) 20%–25% by weight water.

9. The biocide of claim 2 wherein the additive comprises:
   a) 20%–45% by weight mono sodium salt of phosphoric acid, mono (2-ethyl hexyl) ester;
   b) 20%–30% by weight pyrophosphonic acid, bi (2-ethyl hexyl) esters, sodium salts;
   c) 10%–25% by weight polyphosphonic acids, (2-ethyl hexyl) esters;
   d) less than 10% by weight phosphoric acid, bis (2-ethyl hexyl) ester, sodium salt;
   e) less than 3% by weight 2-ethyl hexanol;
   f) less than 5% by weight phosphoric acid, mono and di sodium salts; and
   g) 20%–25% by weight water.

10. An anticorrosive biocide of the peroxide/peracid type wherein the in use solution comprises:
    a) hydrogen peroxide from about 0.004% to about 30% by weight;
    b) peracetic acid from about 0.0003% to less than 55% by weight;
    c) acetic acid from about 0.025% to about 12% by weight;
    d) balance water; and
    e) an anticorrosive additive or additives in an amount of from about 0.001% by weight up to the solubility limit of said additive or additives. Said additive or additives being selected from the group consisting of:
       (i) sodium hydroxide reaction products of an aliphatic alcohol and phosphorous pentoxide
       (ii) a mixture of sodium pentakis (2-ethyl hexyl) triphosphate and phosphoric acid; and
       (iii) potassium perfluoroalkyl sulfonate.

11. The biocide of claim 10 wherein the aliphatic alcohol comprises 2-ethyl hexyl alcohol.

12. The biocide in accordance with claim 11 wherein the additive comprises:
    a) 20%–45% by weight mono sodium salt of phosphoric acid, mono (2-ethyl hexyl) ester;
    b) 20%–30% by weight, pyrophosphonic acid, bi (2-ethyl hexyl) esters, sodium salts;
    c) 10%–25% by weight polyphosphonic acids, (2-ethyl hexyl) esters;
    d) less than 10% by weight phosphoric acid, bis (2-ethyl hexyl) ester, sodium salt;
    e) less than 3% by weight 2-ethyl hexanol;
    f) less than 5% by weight phosphoric acid, mono and di sodium salts; and
    g) 20%–25% by weight water.

13. The biocide in accordance with claim 11 wherein the additive comprises potassium perfluoroalkyl sulfonate.

14. A two-component, anticorrosive, stable, peroxide/peracid biocide, which is shippable in sealed containers, said peroxide/peracid biocide comprising Part A and Part B, wherein Part A comprises:
    a) hydrogen peroxide from about 18% to about 30% by weight;
    b) peracetic acid from about 3% to about 5% by weight;
    c) acetic acid from about 6% to about 10% by weight;

d) balance water;

and wherein Part B comprises an anticorrosive additive or additives, said anticorrosive additive or additives being selected from the group consisting of:

(i) from about 0.005% by weight up to the solubility limit of sodium hydroxide reaction products of an aliphatic alcohol and phosphorous pentoxide;

(ii) from about 0.001% by weight up to the solubility limit of potassium perfluoroalkyl sulfonate; and (iii) from about 0.001% by weight up to the solubility limit of a mixture of sodium pentakis (2-ethyl hexyl) triphosphate and phosphoric acid, disodium;

and wherein Parts A and B when mixed result in a dilution of Part A to a biocidally effective level, and wherein the resulting solution has greater than 0.001% by weight of the additive or additives.

15. The biocide of claim 14 wherein Part A is diluted in Part B from 66 to 80 times.

16. The two-component biocide of claim 14 wherein Part A is mixed with Part B in a ratio of about 58 mls Part A to about 1 gallon Part B.

17. The two-component biocide of claim 14, wherein before the additive of Part B is mixed with water, the additive is dissolved in a quantity of up to about 10% by weight in a water miscible or other compatible solvent.

18. A two-component, anti-corrosive, stable peroxide/peracid biocide, which is shippable in sealed containers, said biocide comprising Part A and Part B wherein Part A comprises:

a) hydrogen peroxide from about 18% to about 30% by weight;

b) peracetic acid from about 3% to about 5% by weight; and c) acetic acid from about 6% to about 10% by weight;

d) balance water; and wherein Part B comprises an additive selected from the group consisting of:

i) sodium hydroxide reaction products of an aliphatic alcohol and phosphorous pentoxide;

ii) a mixture of sodium pentakis (2-ethyl hexyl) triphosphate and phosphoric acid, di sodium; and iii) potassium perfluoroalkyl sulfonate;

and wherein Part A is diluted in Part B from 66 to 80 times to form a final solution having a concentration of the additive from 0.001% by weight to the solubility limit of the additive in the final solution.

19. The biocide in accordance with claim 18 wherein the additive of Part B comprises:

a) 20%–45% by weight mono sodium salt of phosphoric acid, mono (2-ethyl hexyl) ester;

b) 20%–30% by weight pyrophosphonic acid, bi (2-ethyl hexyl) esters, sodium salts;

c) 10%–25% by weight polyphosphonic acids, 2-ethyl hexyl esters, sodium salts;

d) less than 10% by weight phosphoric acid, bi (2-ethyl hexyl) ester, sodium salt;

e) less than 3% by weight 2-ethyl hexanol;

f) less than 5% by weight phosphoric acid, mono and di sodium salts; and g) 20%–25% by weight water.

20. The biocide in accordance with claim 18 wherein the additive of Part B comprises potassium perfluoroalkyl sulfonate.

21. A peroxide/peracid biocide concentrate comprising:

a) hydrogen peroxide from about 18% to about 30% by weight;

b) peracetic acid from about 3% to about 5% by weight;

c) acetic acid from about 6% to about 10% by weight; and d) an anticorrosive additive or additives selected from the group consisting of:

i) sodium hydroxide reaction products of an aliphatic alcohol and phosphorous pentoxide;

ii) a mixture of sodium pentakis (2-ethyl hexyl) triphosphate and phosphoric acid, di sodium, and iii) potassium perfluoroalkyl sulfonate;

wherein, on dilution of the concentrate with water to a biocidally effective level the anticorrosive additive will be present in an amount from about 0.005% by weight up to the solubility limit.

22. An anticorrosive biocide of the peroxide/peracid type wherein the in use solution comprises:

a) hydrogen peroxide from about 0.004% to about 30% by weight;

b) peracetic acid from about 0.0003% to less than 55% by weight;

c) acetic acid from about 0.025% to about 12% by weight;

d) water; and e) an anticorrosive additive or additives in an amount of from about 0.001% by weight up to the solubility limit of said additive or additives, said additive or additives being selected from the group consisting of:

(i) sodium hydroxide reaction products of an aliphatic alcohol and phosphorous pentoxide;

(ii) a mixture of sodium pentakis (2-ethyl hexyl) triphosphate and phosphoric acid; and (iii) potassium perfluoroalkyl sulfonate.

23. The biocide in accordance with either claim 6 or claim 14 wherein the additive comprises:

a) 20%–45% by weight mono sodium salt of phosphoric acid, mono (2-ethyl hexyl) ester;

b) 20%–30% by weight pyrophosphonic acid, bis (2-ethyl hexyl) esters, sodium salts;

c) 10%–25% by weight polyphosphonic acids, 2-ethyl hexyl esters, sodium salts;

d) 20%–25% water;

e) less than 10% phosphoric acid, bis (2-ethyl hexyl) ester, sodium salt;

f) less than 3% 2-ethyl hexanol; and g) less than 5% phosphoric acid, sodium salts, mono and di.

24. The biocide in accordance with either claim 6 or claim 14 wherein the additive is potassium perfluroalkyl sulfonate.

* * * * *